(12) United States Patent
Heuer et al.

(10) Patent No.: US 10,458,642 B2
(45) Date of Patent: Oct. 29, 2019

(54) FAUCET WITH INTEGRATED LIGHT

(71) Applicant: Spectrum Brands, Inc., Middleton, WI (US)

(72) Inventors: Darin Heuer, Anaheim Hills, CA (US); Chasen Beck, Costa Mesa, CA (US); Stephen Blizzard, Mission Viejo, CA (US); Adam William Tracy, Irvine, CA (US)

(73) Assignee: Spectrum Brands, Inc., Middleton, WI (US)

( * ) Notice: Subject to any disclaimer, the term of this patent is extended or adjusted under 35 U.S.C. 154(b) by 12 days.

(21) Appl. No.: 15/843,591

(22) Filed: Dec. 15, 2017

(65) Prior Publication Data

US 2018/0172264 A1 Jun. 21, 2018

Related U.S. Application Data

(60) Provisional application No. 62/434,987, filed on Dec. 15, 2016.

(51) Int. Cl.
| | | |
|---|---|---|
| *F21V 33/00* | (2006.01) | |
| *A61L 2/10* | (2006.01) | |
| *E03C 1/04* | (2006.01) | |
| *E03C 1/05* | (2006.01) | |
| *F21S 10/02* | (2006.01) | |
| *F21V 23/04* | (2006.01) | |

(52) U.S. Cl.
CPC ............ *F21V 33/004* (2013.01); *A61L 2/10* (2013.01); *E03C 1/0404* (2013.01); *E03C 1/057* (2013.01); *F21S 10/02* (2013.01); *F21V 23/0485* (2013.01); *F21V 23/0471* (2013.01)

(58) Field of Classification Search
CPC ...................................... F21V 33/004
USPC ............................................. 4/678
See application file for complete search history.

(56) References Cited

U.S. PATENT DOCUMENTS

| | | |
|---|---|---|
| 6,805,458 B2 | 10/2004 | Schindler et al. |
| 7,008,073 B2 | 3/2006 | Stuhlmacher, II |
| 7,270,748 B1 | 9/2007 | Lieggi |
| 7,396,459 B2 | 7/2008 | Thorpe |
| 7,434,960 B2 | 10/2008 | Stuhlmacher, II et al. |
| 9,757,486 B2 | 9/2017 | Dobrinsky et al. |
| 2004/0032749 A1 | 2/2004 | Schindler et al. |
| 2008/0291660 A1 | 11/2008 | Gautschi et al. |

(Continued)

FOREIGN PATENT DOCUMENTS

| | | |
|---|---|---|
| DE | 10 2005 015 129 A1 | 5/2006 |
| EP | 1 703 024 A1 | 9/2006 |

(Continued)

OTHER PUBLICATIONS

International Search Report and Written Opinion for Application No. PCT/US2017/066455 dated May 24, 2018.

(Continued)

*Primary Examiner* — Lori L Baker
(74) *Attorney, Agent, or Firm* — Merchant & Gould P.C.

(57) ABSTRACT

A faucet may be used to deliver water in a temperature and volume controlled manner. The faucet may also deliver light through the use of an integrated light fixture. The light fixture may emit at least one of visible and ultraviolet light. The light fixture may be selectively activated to display a number of types of light, intensities of light, and/or light colors. The activation of the light may be done through a touch sensor, optical sensor, and/or audio sensor.

21 Claims, 17 Drawing Sheets

(56) References Cited

U.S. PATENT DOCUMENTS

2015/0101121 A1  4/2015 Burgo, Sr. et al.
2016/0332894 A1  11/2016 Knight et al.

FOREIGN PATENT DOCUMENTS

WO    01/34917 A1    5/2007
WO   2004/051010 A2  6/2007
WO   2007/129174 A1  11/2007

OTHER PUBLICATIONS

Invitation to Pay Additional Fees with Partial International Search for Application No. PCT/US2017/066455 dated Mar. 27, 2018.

FAUCET WITH INTEGRATED LIGHT

CROSS REFERENCE TO RELATED APPLICATION

The present patent application claims the benefit of U.S. Provisional Patent Application Ser. No. 62/434,987, filed Dec. 15, 2016, which application is hereby incorporated by reference in its entirety.

BACKGROUND

Faucets are commonplace in bathroom and kitchen environments. They allow temperature and volume controlled dispensing of potable water in a convenient manner. Oftentimes faucets are installed in areas with limited natural lighting. Either through lack of windows, location in the dwelling, or limited light fixtures, it can often be difficult for a user to clearly see below the faucet. Further, kitchen environments, specifically sinks with faucets, often host a plurality of undesirable germs and bacteria originating from raw foods, mold, and other general-purpose use of the sink.

Certain tasks performed in proximity of faucets require greater attention to detail which benefits from increased lighting. For example, cleaning spot stains from clothing, inspecting food following washing, or even reading fine print for recipes are all situations where increased lighting is desired. There have been efforts to address this need, including use of lamps or added light fixtures in the room. Adding light fixtures to the room presents additional problems as it increases the clutter in the environment and adds considerable expense. Additional wiring or installation efforts are also required. There have also been recent attempts at adding lighting directly to the water stream. This provides an added aesthetic appeal, but does little to illuminate the surrounding area in a useful manner.

While certain tasks performed in the sink need more light, it is also known that the sink can accumulate a plethora of pathogens. Efforts to eliminate these pathogens have historically included spot cleaning with soap or using bleach or other similar chemical solutions. However, not only can these methods be ineffective, but use of such chemicals can be dangerous and their effectiveness is reliant on the user. It is known that ultraviolet light (UV) can mitigate the spread of bacteria, viruses, and other pathogens. However, cleaning a surface such as a sink using a handheld UV light can be cumbersome and daunting to the user.

Therefore, improvements in sink lighting and disinfecting is need.

SUMMARY

The present disclosure relates generally to faucets. In one possible configuration, and by non-limiting example, a faucet with an integrated lighting fixture is disclosed.

In one embodiment of the present disclosure, a faucet is disclosed. The faucet includes a body that has a first end and a second end. The first end is securable to a surface and the second end is spaced from the first end. The faucet includes a neck that has a first end and a second end. The first end of the neck is coupled to the second end of the body and the second end of the neck is cantilevered from the body. The faucet includes a light fixture secured in an exterior portion of the neck between the first end and the second end of the neck. The faucet includes a spray head coupled to the second end of the neck.

In another embodiment of the present disclosure, a faucet is disclosed. The faucet includes a body that has a first end and a second end. The first end is securable to a surface and the second end is spaced from the first end. The faucet includes a neck that has a first end and a second end. The first end of the neck is coupled to the second end of the body and the second end of the neck is cantilevered from the body. The neck is movable with respect to the body. The faucet includes a spray head coupled to the second end of the neck, opposite the body. The faucet includes a light fixture secured to at least one of an exterior portion of the body, neck, and spray head. The faucet includes at least one input device that is configured to receive input from a user. Upon receipt of an input, the input device activates the light fixture.

In another embodiment of the present disclosure, a faucet is disclosed. The faucet includes a body with a base that is configured for attachment to a counter. The body includes a top, opposite the base, suspended above the counter. The faucet includes an input device that is configured to receive input from a user regarding at least one of a water volume and a water temperature. The faucet includes a neck that has a first end attached to the top of the body, a mid-section that is defined by a curvature, and a second end opposite the first end. The faucet includes a spray head attached to the second end of the neck. The spray head is configured for detachment from the neck. The faucet includes a light fixture secured to the neck and oriented facing the counter between the body and the spray head.

In another embodiment of the present disclosure, a faucet may include a body secured to a counter top. The counter top forms a planar surface, or a plane. The faucet includes a body that has a first end with an opposing second end suspended above the counter. A first end of a neck pivotally connects to the second end of the body. The neck includes a second end opposite the first end of the neck. The second end of the neck is cantilevered from the body.

In another embodiment of the present disclosure, an input device such as a lever or other valve controller may be included to receive input from a user regarding at least one of a water volume and a water temperature. This may allow the user to determine temperature and/or flow rate of the water delivered by the faucet. Alternatively, there may not be any manual valve, but the input device may receive audio, visual, or any other type of commands.

In another embodiment of the present disclosure, within an exterior portion of the neck, is an opening formed in a portion of the neck that faces the plane of the counter. A light fixture is secured within the opening of the neck and includes a light within the opening. A spray head is attached to the second end of the neck and may be removed from the neck. When the spray head is removed from the neck, it is retractably tethered to the faucet.

In another embodiment of the present disclosure, the light fixture may be selectably activated to illuminate at a plurality of user-selectable intensity levels. In some examples, the light fixture is a plurality of light emitting diodes spaced apart along a length of the neck within the opening in the neck and each intensity level corresponds to a different number of light emitting diodes being energized and a different amount of light output. In some examples, the light fixture can emit at least one of visible light and UV light.

In another embodiment of the present disclosure, in order to activate the light fixture, any one of a touch on a surface of the faucet, a sensed motion by a proximity sensor, or a sensed gesture by a sensor may activate the light. The emitted light may also be projected downward, towards the plane of the counter, as the light fixture is in a portion of the neck that faces the plane of the counter. The neck may also be curved in an arc or other shape with the light fixture residing in the curved portion.

A variety of additional aspects will be set forth in the description that follows. The aspects can relate to individual features and to combinations of features. It is to be understood that both the foregoing general description and the following detailed description are exemplary and explanatory only and are not restrictive of the broad inventive concepts upon which the embodiments disclosed herein are based.

BRIEF DESCRIPTION OF THE DRAWINGS

The following drawings are illustrative of particular embodiments of the present disclosure and therefore do not limit the scope of the present disclosure. The drawings are not to scale and are intended for use in conjunction with the explanations in the following detailed description. Embodiments of the present disclosure will hereinafter be described in conjunction with the appended drawings, wherein like numerals denote like elements.

Corresponding reference characters indicate corresponding parts throughout the several views. The exemplifications set out herein illustrate an embodiment of the invention, and such exemplifications are not to be construed as limiting the scope of the invention in any manner.

DETAILED DESCRIPTION

Figure 1:
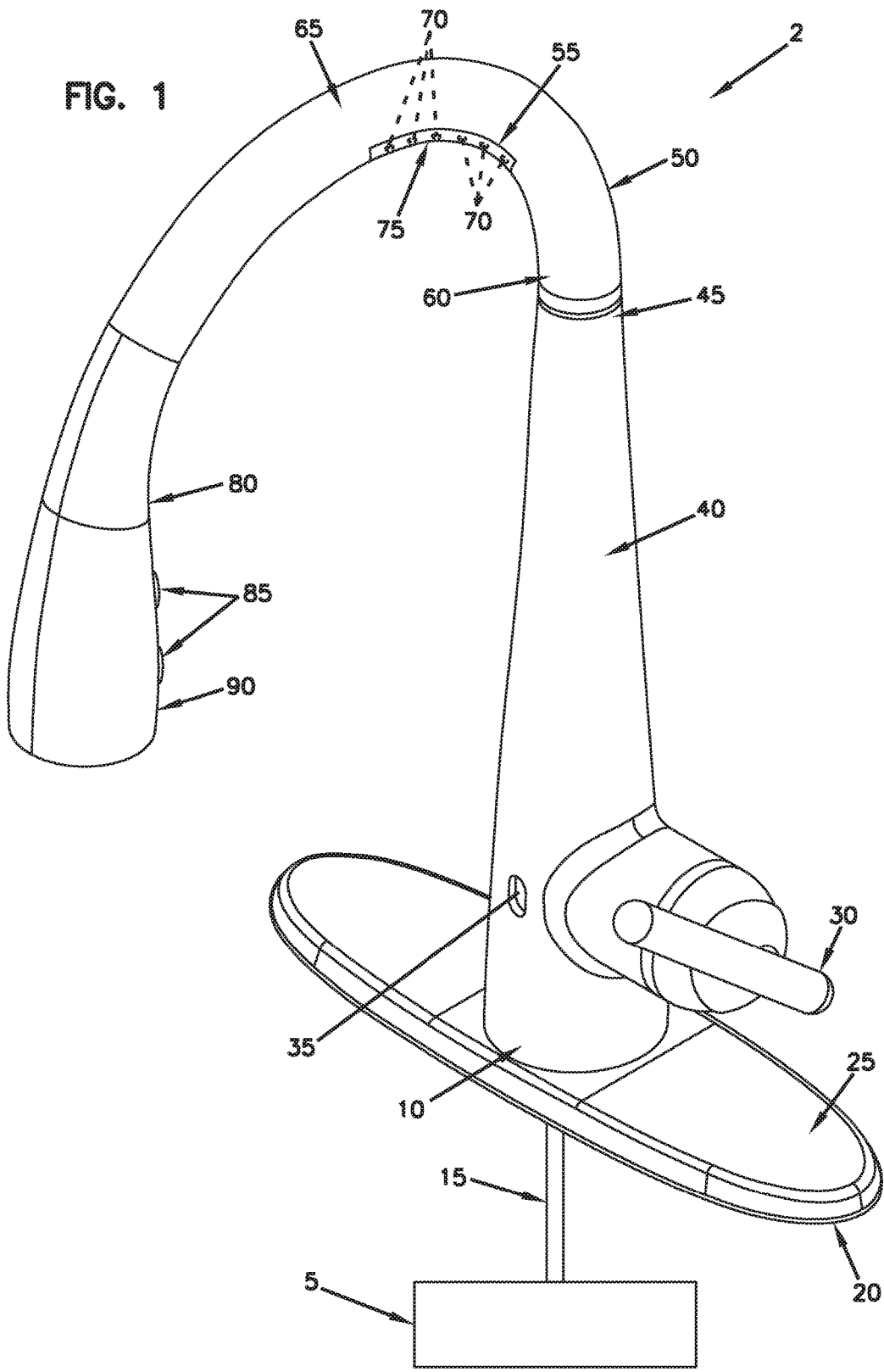
FIG. 1 is a perspective view of a faucet with integrated lighting, according to one embodiment of the present disclosure.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

The faucet disclosed herein includes a plurality of advantages. The faucet includes a light fixture that is configured to emit at least one of visible light and UV light. In some examples, the light fixture can emit visible light and UV light separately or together. When emitting visible light, the light fixture is configured to illuminate an area under the faucet, such as the counter and/or sink, to improve lighting for tasks performed in the area under the faucet. When emitting ultraviolet light, the light fixture is configured to illuminate the area under the faucet in germicidal UV light to clean the area under the faucet.

Figure 2:
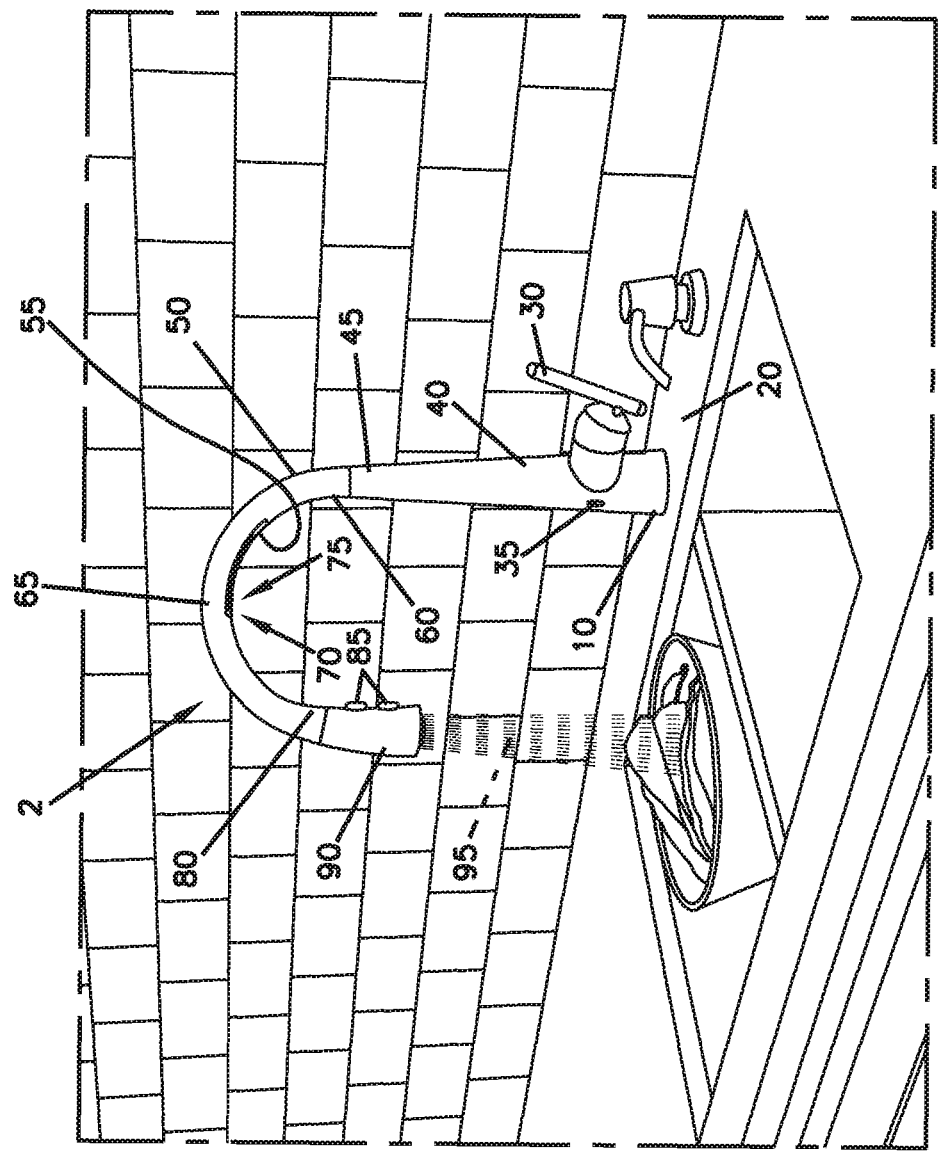
FIG. 2 is a perspective view of the faucet of FIG. 1 in a typical installation with water running.
Figure 3:
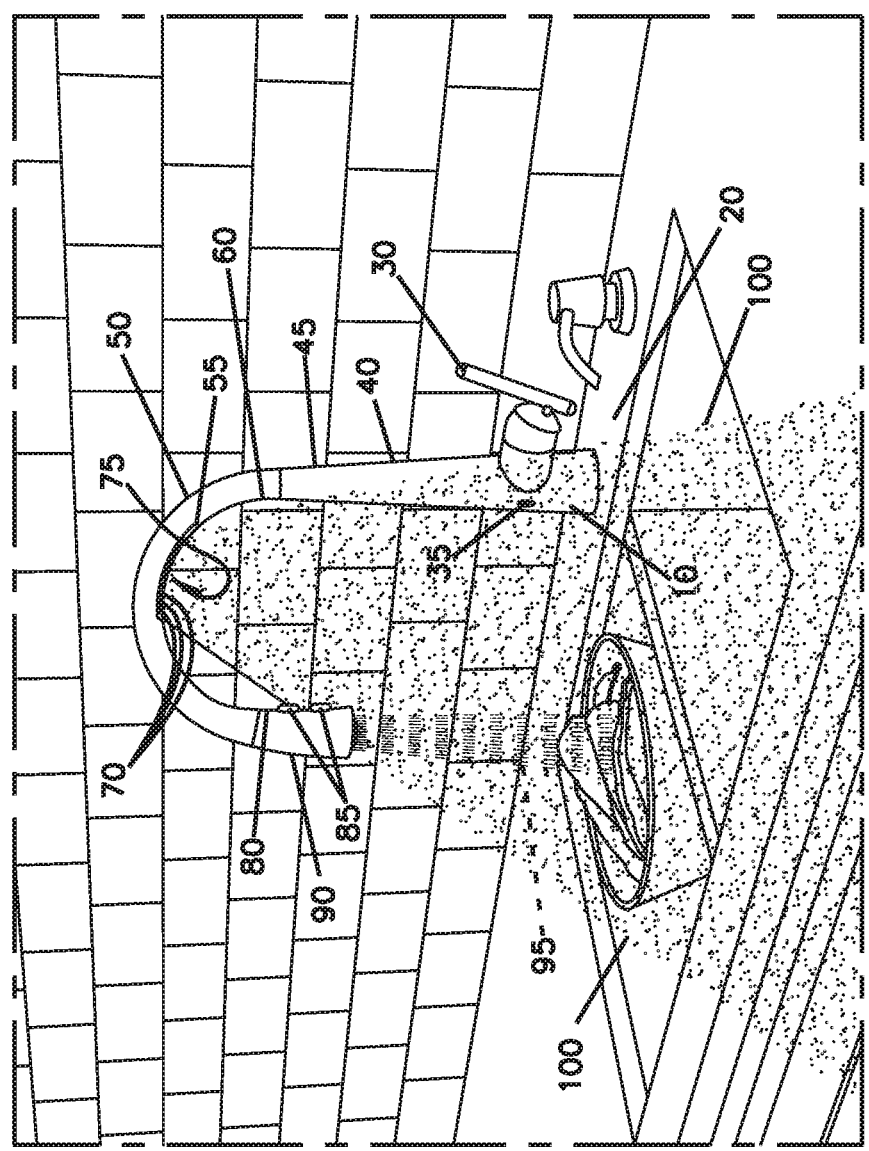
FIG. 3 is a perspective view of the faucet of FIG. 1 in a typical installation with the integrated lighting activated.

FIGS. 1-3 show a faucet 2 according to an embodiment of the present disclosure. The faucet 2 includes a controller 30, which acts as an input device for receiving user input. The user input may include physical manipulation of the controller 30 through rotation and pivoting of the controller. The manipulation of the controller 30 allows the user to select a desired amount of volume of water from a water supply 5. The user may also select the desired temperature of the water from the water supply 5. While the controller 30 is shown in the form of a lever, it is conceived that a hands-free input device (e.g., a sensor not require physical manipulation of the controller 30) may also be used. For example, a voice-activated sensor or an optical sensor may be employed allowing the user to set the desired flow rate and temperature of water through voice commands or through motion. A touch sensor (e.g., a capacitive sensor), voice-activated (e.g., audio sensor such as a microphone), or proximity sensor (e.g., infrared or ultrasonic sensor) may also be used to activate and control a light fixture 75 function. Alternatively, a touch sensor may be employed allowing a simple touch, tap, or swipe on the faucet to determine the desired flow rate, the temperature of the water, and the light fixture 75 function.

The controller 30 is mounted to a body 40, which is preferably upright with respect to a counter 20. The counter 20 forms a plane that supports the body 40. An optional deck plate 25 may be used to conceal any holes or imperfections in the counter 20 surface. A first end 10 of the body is configured to secure to the counter 20 and support a second end 45 of the body 40 above the counter 20.

A neck 50 attaches to the second end 45 of the body 40 and cantilevers the second end 80 of the neck 50 away from the body 40. The neck 50 is shown with a curved portion 65 that forms an arc. In some examples, the neck 50 may be planar or any other shape. At a second end 80 of the neck 50, a spray head 90 is coupled. The spray head 90 dispenses water in a spray pattern 95. In some examples, the spray pattern 95 is selectable through manipulation of spray buttons 85. Preferably, the spray head 90 is detachable from the second end 80 of the neck 50. While detached, the spray head 90 remains tethered to the faucet 2 through a water supply line 15, which is disposed within the body 40 and neck 50.

The faucet 2 provides lighting to the area through the use of the light fixture 75 located in an exterior portion of (i.e. outside, not internally) the neck 50. The light fixture 75 may also be located on the body 40 or the spray head 90. In some examples, the neck 50 includes an opening 55 along a length of the neck 50 that faces the counter 20. Orienting the light fixture 75 on part of the neck 50 that faces the counter 20 allows light to be projected downwards towards a sink or other workspace where lighting may be needed. In some examples, the light fixture 75 is embedded into the neck 50 and hermetically sealed or water resistant. Light emitting diodes 70 are preferably used to emit lighting as they consume little energy and have long lifespans. Using multiple light emitting diodes 70 along the length of the opening 55 also allows the user to fine-tune the amount of light emitted. Preferably, the neck 50, which houses the light fixture 75, may pivot about the body 40 and allow the user to aim the output light 100 and spray pattern 95 in a desirable area. In some examples, the light fixture 75 is configured to emit visible light, infrared light, and/or UV light.

For example, a second input device 35, such as an infrared or ultrasonic sensor, audio sensor, or other proximity detector, may be included in the body 40. The second input device 35 may receive input from the user. Following detection of the prerequisite input, the light emitting diodes 70 may be energized to produce light 100 shown in FIG. 3. Different amounts of individual light emitting diodes 70 may be selectively energized through different input sensed by the second input device 35. In some examples, visible light is emitted from the light fixture 75 when a first input sensed by the second input device 35. In other examples, UV light is emitted from the light fixture 75 when a second input is sensed by the second input device 35. The sensed input may be in the form of a hand gesture, a touch, a voice command, or the like.

The light fixture 75 has at least an ON state and at least an OFF state. When in the ON state, the light fixture emits light and when in the OFF state the light fixture 75 does not emit light. In some examples, the output light 100 may also be selectively adjusted. In some examples, the output light 100 can be adjusted to display different color temperatures of visible light such as a cooler tone or a warmer tone. In other examples, the output light 100 may also be adjusted for different intensity levels by controlling the amount of electricity used to energize the light emitting diodes 70, such as with a dimmer. The electricity may be provided to the light fixture 75 either through an integrated battery in the light fixture 75 or through household line voltage.

The faucet 2 may also include additional light fixtures 75 or position the opening 55 for the light fixture 75 in another location of the faucet 2. In some examples, the faucet 2 can include an individual light fixture for at least visible light and UV light. In some examples, the separate light fixtures can communicate with one another and operate together. In some examples, the light fixture 75 can be remotely operated. For examples, the light fixture 75 can be operated via a switch located on a wall. The controller 30 may also be in another form or not used as the faucet 2 may be touch activated, remote activated, or voice activated.

Figure 4:
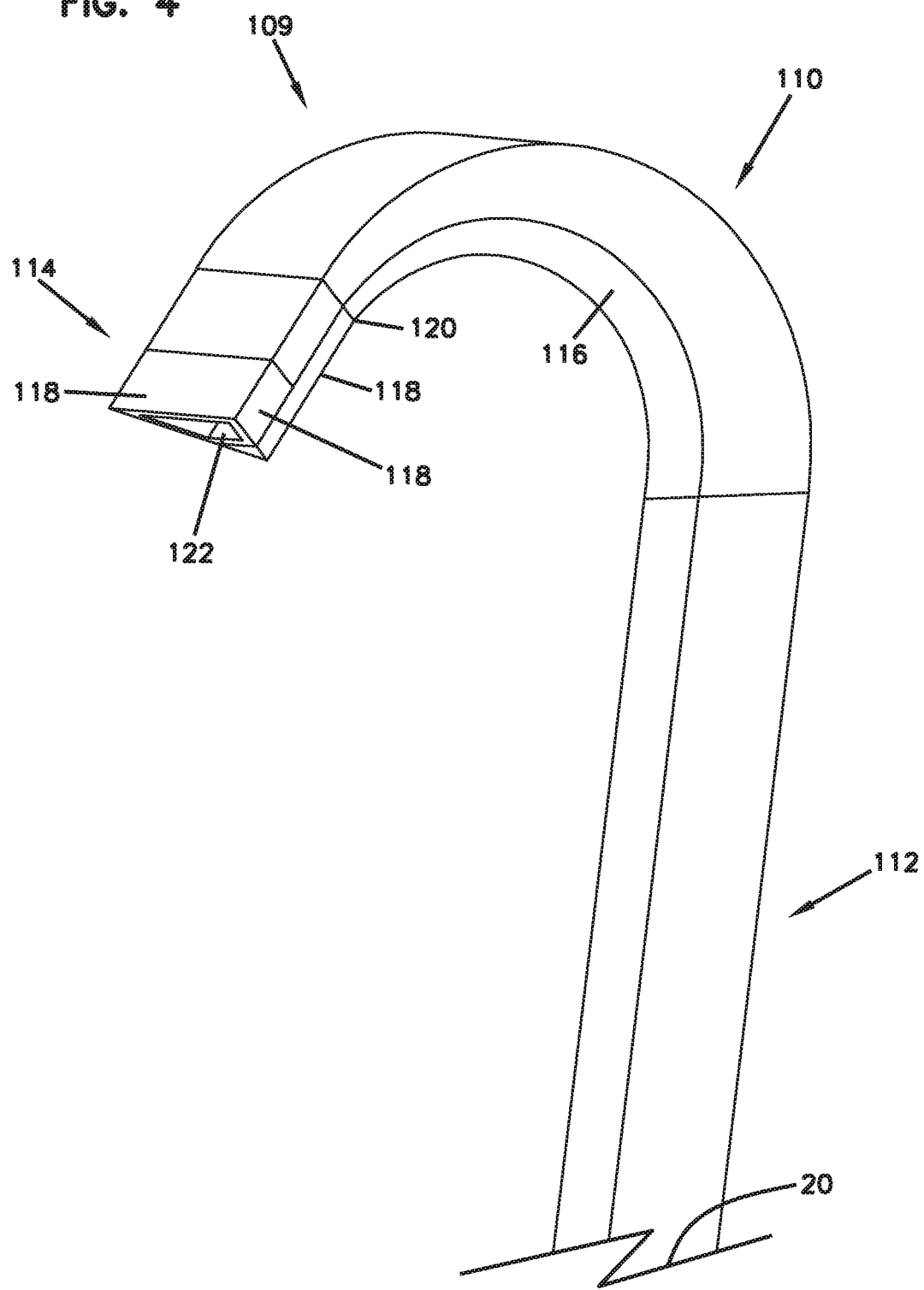
FIG. 4 is a perspective view of an alternative embodiment of a faucet, according to one embodiment of the present disclosure.
Figure 5:
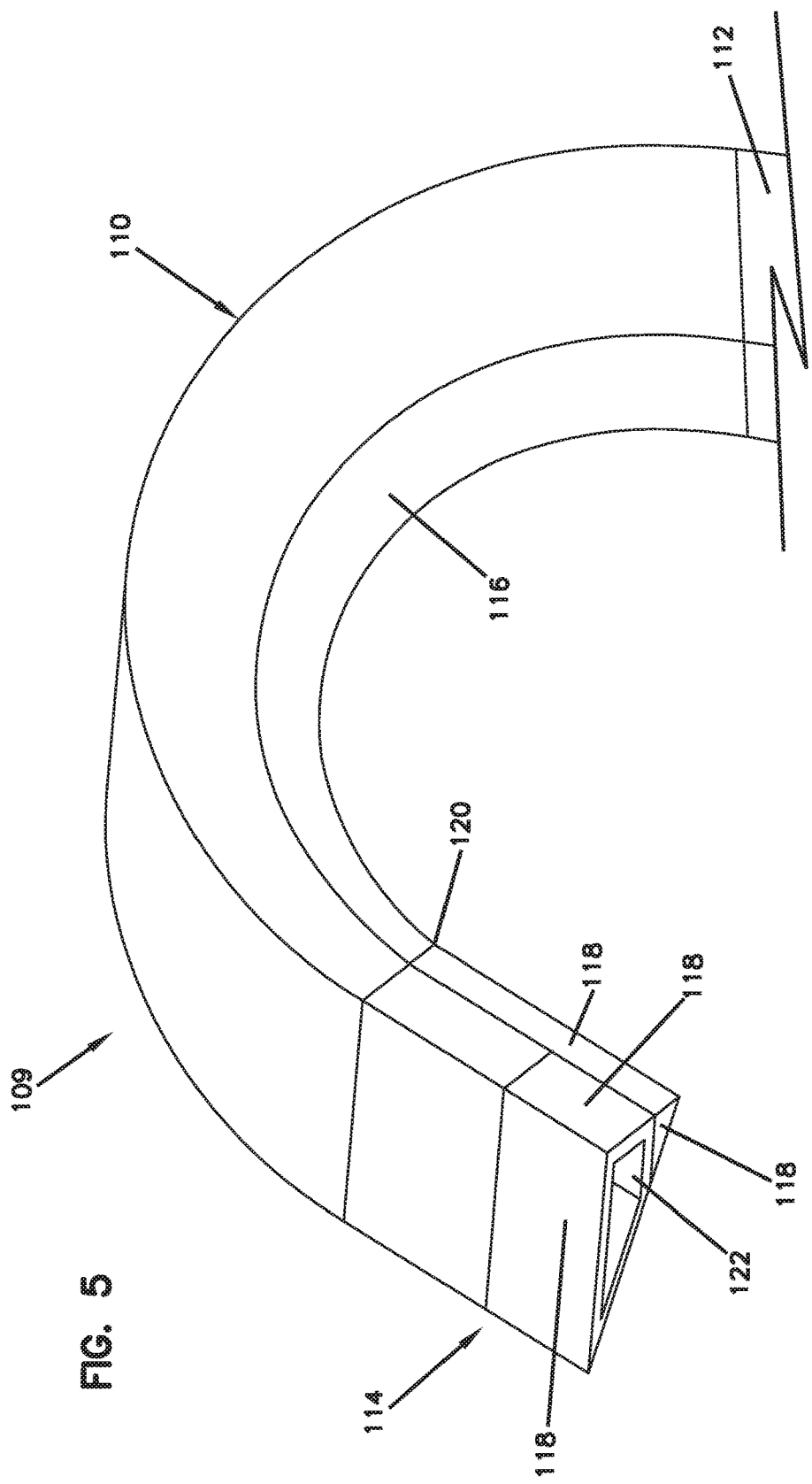
FIG. 5 is a close-up perspective view of the faucet of FIG. 4.
Figure 6:
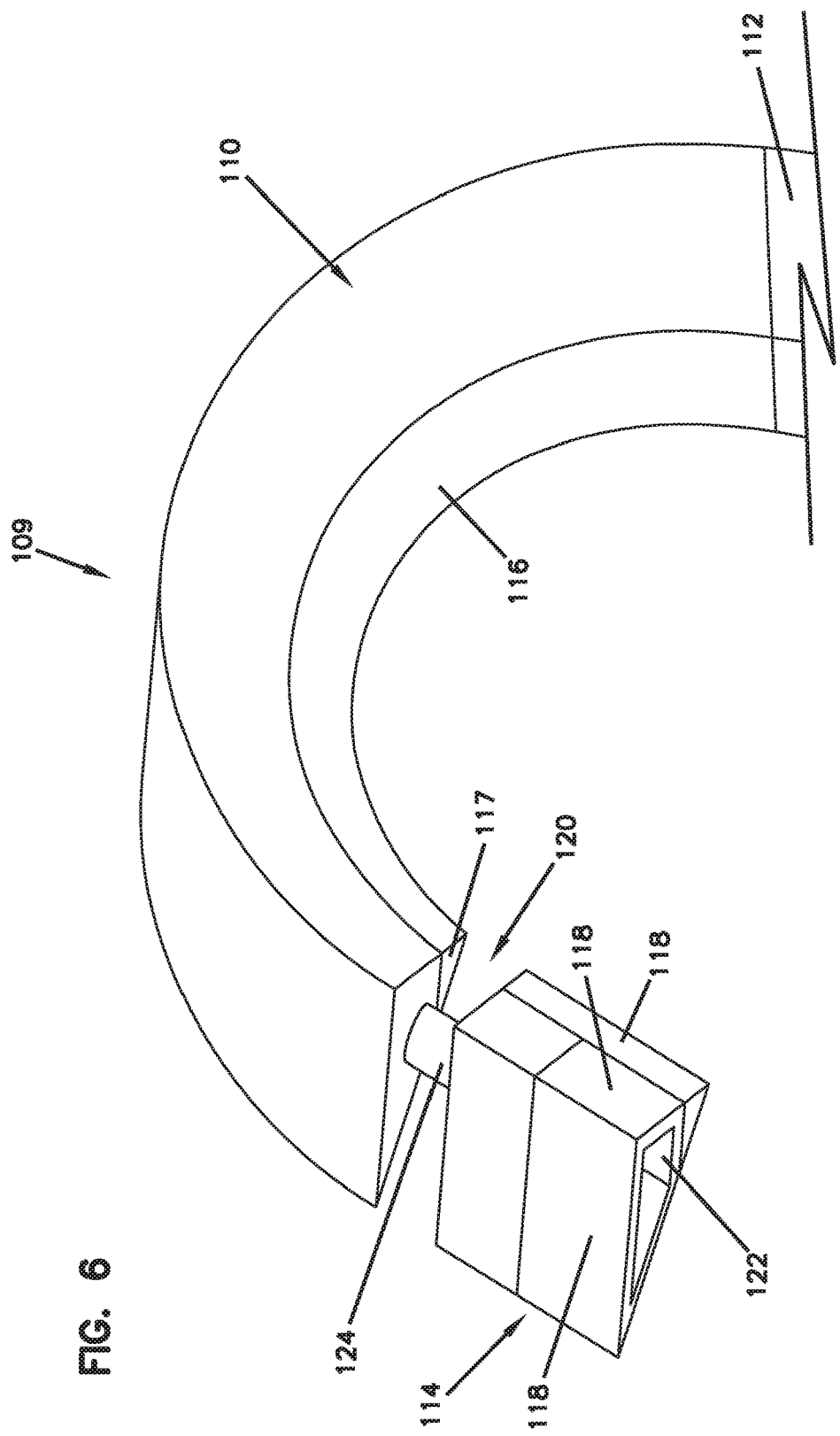
FIG. 6 is a close-up perspective view of the faucet of FIG. 4 with the spray head detached.

Referring now to FIGS. 4-6, an alternative embodiment of the invention is shown. A faucet 109 is substantially similar to the previously discussed faucet 2 of FIGS. 1-3 in that it includes a body 112, a neck 110, and a spray head 114. While a control lever is not shown, a similar control may be used, or the faucet may be sensor controlled (i.e., touch, voice, motion) as well. The faucet 109 may deliver water and lighting and be controlled similar the previously discussed faucet 2. The faucet 109 may also be secured to the counter 20.

The faucet 109 includes a light fixture 116 that may extend along the body 112 or terminate at the body 112. The light fixture 116 is preferably made of a translucent material such as a clear plastic that acts as a light pipe. The light pipe can transmit the light throughout the length of the light pipe in the same manner as an optical fiber.

In the depicted example, the light fixture 116 is located on the neck 110 and all the related light emitting diodes are similarly located on/in the neck 110 so that light can emit from an exterior of the neck 110. As depicted, the spray head 114 does not include any light emitting diodes. As the spray head 114 is detachable, power-transmitting devices such as wires are not required to pass from the neck 110 to the spray head 114 due to the nature of the light pipe. Light originating from the light fixture 116 on the neck can be transmitted through the light pipe and pass a joint 120 where the spray head 114 meets the neck 110. The light can then enter the spray head light pipe 118 when the spray head 114 is docked to the neck 110 as shown in FIG. 4.

The spray head light pipe 118 may surround a water spout 122 transmitting light into exiting water, thereby allowing the water stream to act as a light pipe, or the spray head light pipe 118 may keep the emitted light separate from the water.

Once the spray head 114 is detached from the neck 110, as shown in FIG. 6 with a water supply line 124 tethering the spray head 114 to the neck 110, the light within the light fixture 116 will not transmit from an end point 117 of the light pipe into the spray head light pipe 118. In this situation, the spray head light pipe 118 will not emit light. It is possible to place light emitting diodes within the spray head 114, but as previously discussed, it would require a power source within the spray head 114. The alternative embodiment faucet 109 allows light to emit from the spray head 114 without including any light emitting diodes or power supply within the spray head 114.

It is also envisioned that the light emitting diodes may be placed anywhere in the faucet 109 such as on/in the body 112 or even remote from the faucet 109. The light pipe may be any length transmitting the light from any source below or above the counter 20.

Figure 7:
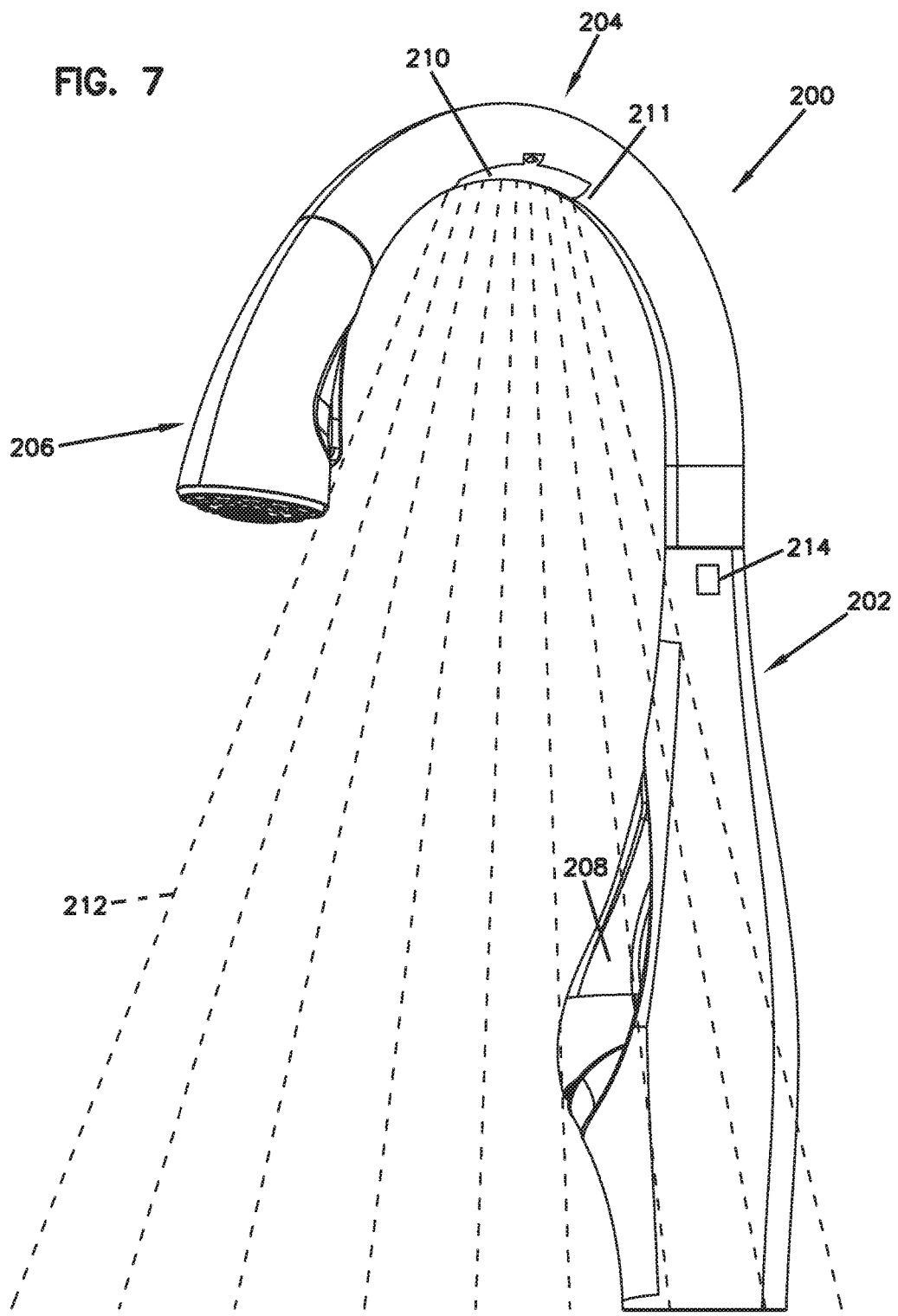
FIG. 7 is a perspective view of a faucet with integrated lighting, according to one embodiment of the present disclosure.
Figure 8:
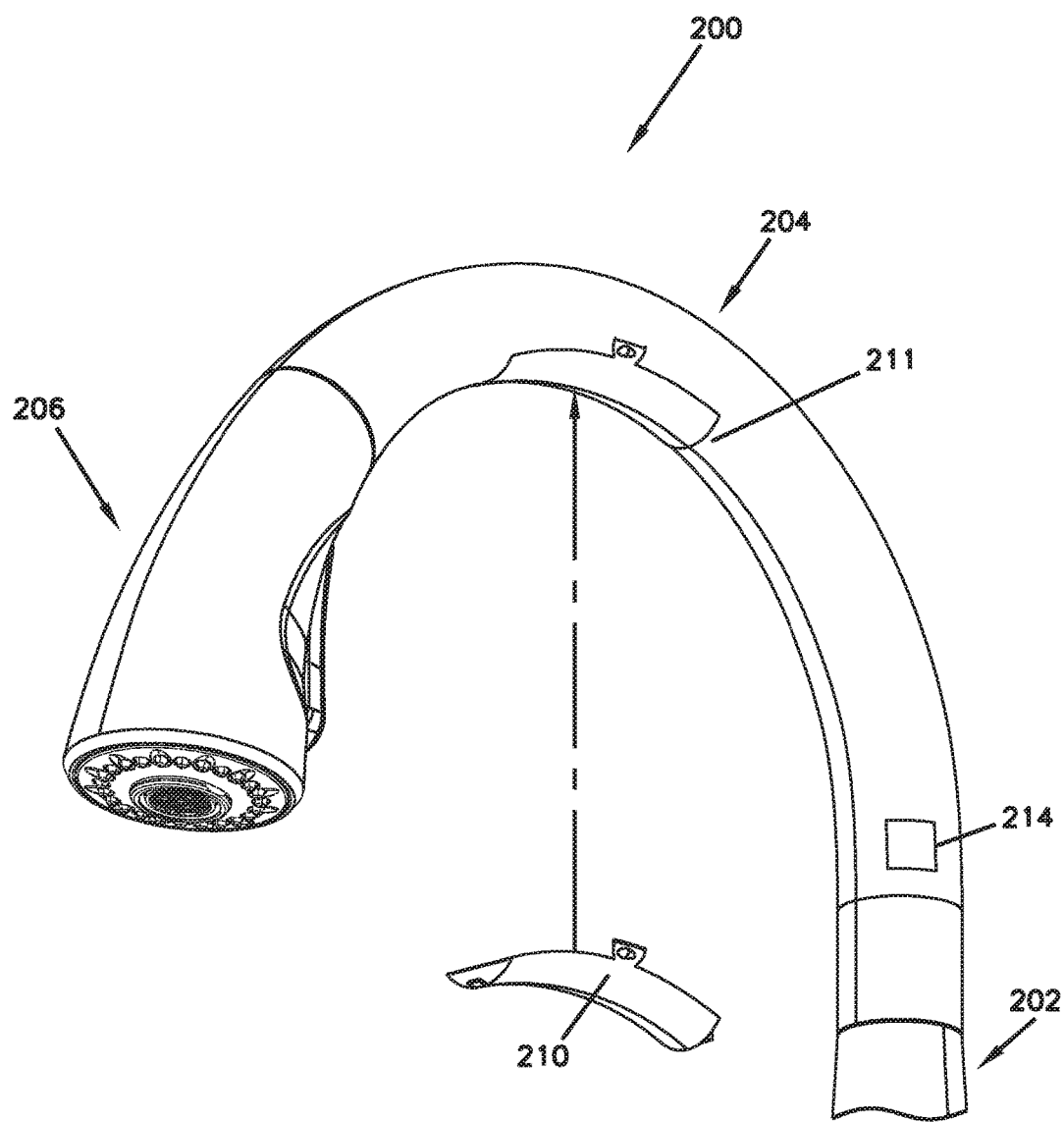
FIG. 8 is perspective view of a portion of the faucet of FIG. 7, with a light fixture removed.
Figure 9:
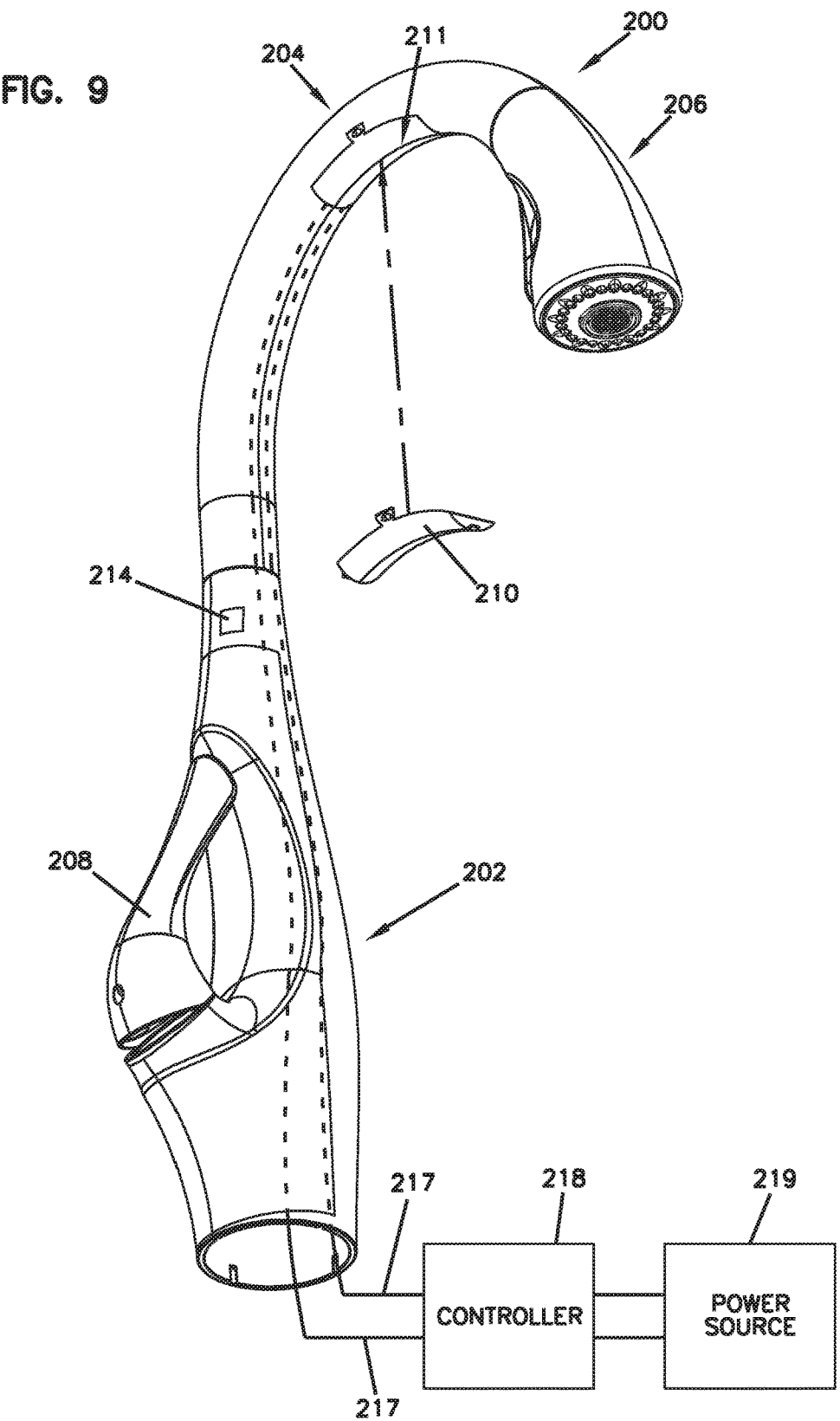
FIG. 9 is another perspective view of the faucet of FIG. 7.

FIGS. 7-9 show a faucet 200 according to another embodiment of the present disclosure. The faucet 200 is substantially similar to the faucets 2, 109 disclosed above. The faucet 200 includes a body 202, a neck 204, a spray head 206, an optional first input device 208, and a light fixture 210. In some examples, the faucet 200 does not include a first input device 208 and is instead controlled by sensor (i.e., touch, voice, motion, etc.). The faucet 200 is configured to deliver water and lighting and be controlled similar the previously discussed faucets 2, 109. The faucet 200 is securable to a counter using an optional deck plate and mounting hardware (not shown).

The light fixture 210 is configured to be positioned within a portion of the faucet 200 at a mounting location 211. As shown in FIG. 8, the light fixture 210 can be removably mounted to faucet 210. In the depicted example, the light fixture 210 is positioned within an exterior portion of the neck 204 of the faucet 200 so that light can emit from the exterior of the neck 204. In some examples, the mounting location 211 is an opening in the neck 204. In some examples, the light fixture 210 is configured to emit at least one of visible light and UV light in a coverage pattern 212. In some examples, the light fixture 210 can emit both visible light and UV light, either at the same time or individually, based on particular inputs received by the user.

When emitting visible light, like the light fixtures 75, 116 described above, the light fixture 210 can be configured to emit a variety of different colors, intensities, and patterns of the visible light. In some examples, the visible light can be a version of white light with an intensity range that is suited for performing tasks. In other examples, the visible light can be a warm version of visible light with an intensity range suited for ambient lighting. In some examples, the light fixture 210 can emit a dim light in order to aid a user in locating the faucet 200 in dimly lit environments. In some examples, the light fixture 210 can emit light that has a color different from white. In some examples, the color of the light emitted from the light fixture can be changed to the user's preference (e.g., to match a particular kitchen environment or personal preference). In some examples, the light fixture 210 can include light emitting diodes.

When emitting UV light, the light fixture 210 is configured to perform a cleaning function. In some examples, the UV light selectively emitted from the light fixture 210 is contained within the UV-C spectrum and is germicidal. In some examples, the UV light emitted from the light fixture 210 can have a wavelength between about 100 nm and 350 nm. In some examples, the UV light emitted from the light fixture 210 can have a wavelength between 200 nm and 325 nm. In some examples, UV light emitted from the light fixture 210 can have a wavelength between 250 nm and 300 nm. In some examples, the light fixture 210 includes light emitting diodes that are capable of producing UV-C light (i.e., UV-C LEDs). In some examples, the light fixture 210 includes a mercury vapor lamp for emitting UV light.

The light fixture 210 can be directional to specifically aim the light pattern 212 (either visible or UV) in a particular direction. For example, the light pattern 212 for visible light can have a cover a larger area than the light pattern for UV light emitted from the light fixture 210.

In some examples, the light fixture 210 is controlled via the first input device 208. For example, the light fixture 210 can be activated between ON and OFF states at the same time the user starts the flow of water through the faucet 200 via the first input device 208. In other examples, the light fixture 210 can be controlled via a second input device 214, similar to the second input device 35, as described above. The second input device 214 can be positioned anywhere on the body 202, neck 204, and/or spray head 206. The first input device 208 and the second input device 214 can be configured to communicate with one another to control particular actions of the faucet 200. For example, the second input device 214 can trigger the first input device 208. In some examples, the second input device 214 can override the first input device 208. For example, if the second input device 214 receives an input from a user that corresponds with turning on both the light fixture 210 and the water flow from the faucet 200, the second input device 214 can override the first input device 208, if it is positioned in an OFF position, to turn on water flow from the faucet 200.

In some examples, as shown in FIG. 9, a controller 218 can be in communication with the light fixture 210 (either via a wired connection or a wireless connection) to control the operation of the light fixture 200. As shown, the controller 218 is connected to a power source 219 such as a battery or to household line voltage. As shown, the light fixture 210 is connected to the power source 219 via power leads 117. In some examples, the first input device 208 and/or the second input device 214 are in communication with the controller 218. In some examples, the controller 218 can be a microcontroller that includes a processor and on-board memory.

In some examples, the controller 218 and/or power supply 219 can be mounted remotely from the faucet 200, such as under a counter or in a cabinet. In other examples, the controller 218 and/or the power supply 219 is mounted within the faucet 200 and/or within the light fixture 210.

The controller 218 can control the operation of the light fixture 210 based on inputs received at the first and/or second input devices 208, 214. The first and/or second input devices 208, 214 can be configured to communicate signals to the controller 218 that are representative that an input has been sensed and/or received by the first and second input devices 208, 214. The controller 218 can control when, how, and for how long the light fixture 210 is activated based on preprogrammed data and/or inputs received at the first and/or second input devices 208, 214. For example, based on the input received at the first and/or second input devices 208, 214, the controller 218 can control whether the light fixture 210 emits visible light, UV light, or both. In some examples, the controller 218 can also be in communication with the faucet 200 to control the operation of the faucet 200 (such as water volume and temperature) based on signals received from the first and/or second input devices 208, 214.

In some examples, the controller 218 can provide for a variety of different operation modes of the light fixture 210. The operation modes can control the behavior of when, how, and for how long the light fixture emits visible and/or UV light. In some examples, the controller 218 can have a timer mode, where the controller 218 automatically deactivates the light fixture 210 after a preset amount of time has elapsed. In some examples, the timer mode can be based on input received, or not received, at the first and/or second input devices 208, 214. For example, if the controller 218 does not receive a signal from the second input device 214 (e.g., no motion, touch, voice, etc.) after a predetermined amount of time has elapsed, the controller 218 will automatically deactivate the light fixture 210, thereby turning it to the OFF state. This timer mode can be used by the controller 218 to automatically deactivate the light fixture 210 when either visible light and/or UV light is emitted from the light fixture 210.

Alternatively, the controller 218 can have a cleaning mode in which the controller 218 automatically deactivates the light fixture 210 to prevent the light fixture 218 from emitting UV light when a signal is received from the first and/or second input devices 208, 214 that is representative that an input has been received. For example, the controller 218 automatically deactivates the light fixture 210 to prevent the light fixture 210 from emitting UV light when the first and/or second input devices 208, 214 senses the presence of a user, such as by motion, voice, touch, or additional input.

Figure 10:
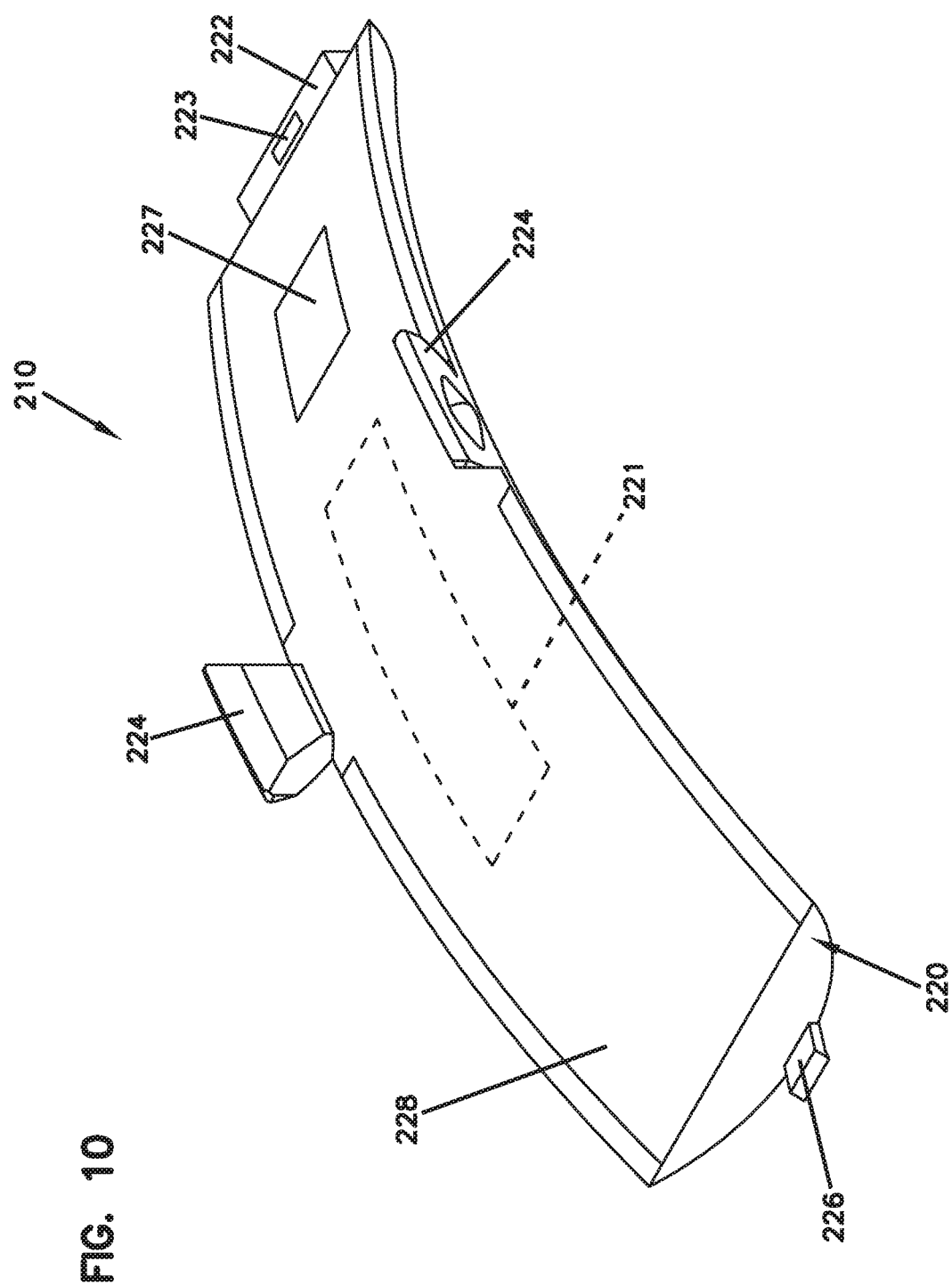
FIG. 10 is a perspective view of the light fixture of FIG. 8.
Figure 11:
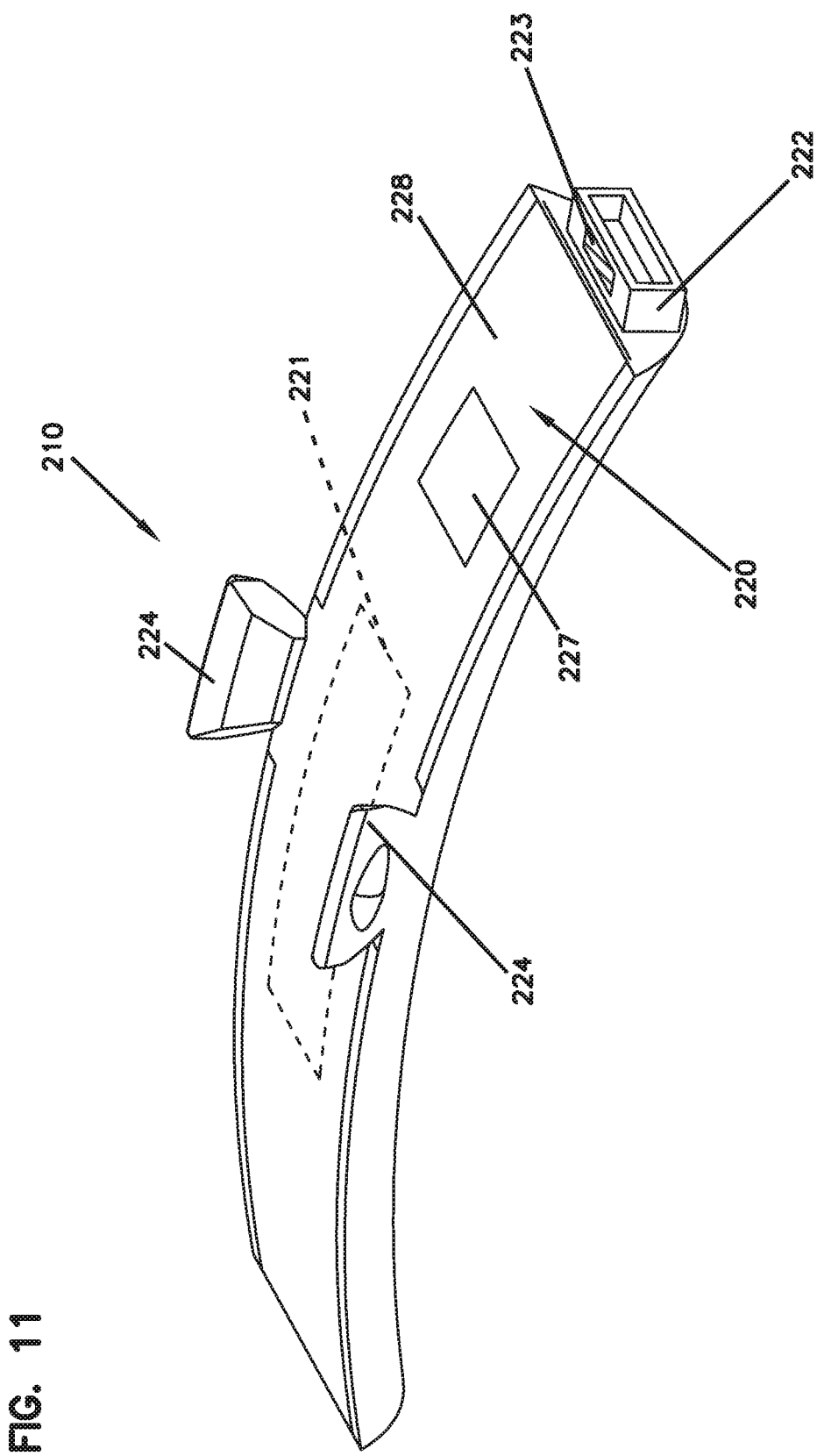
FIG. 11 is another perspective view of the light fixture of FIG. 8.
Figure 12:
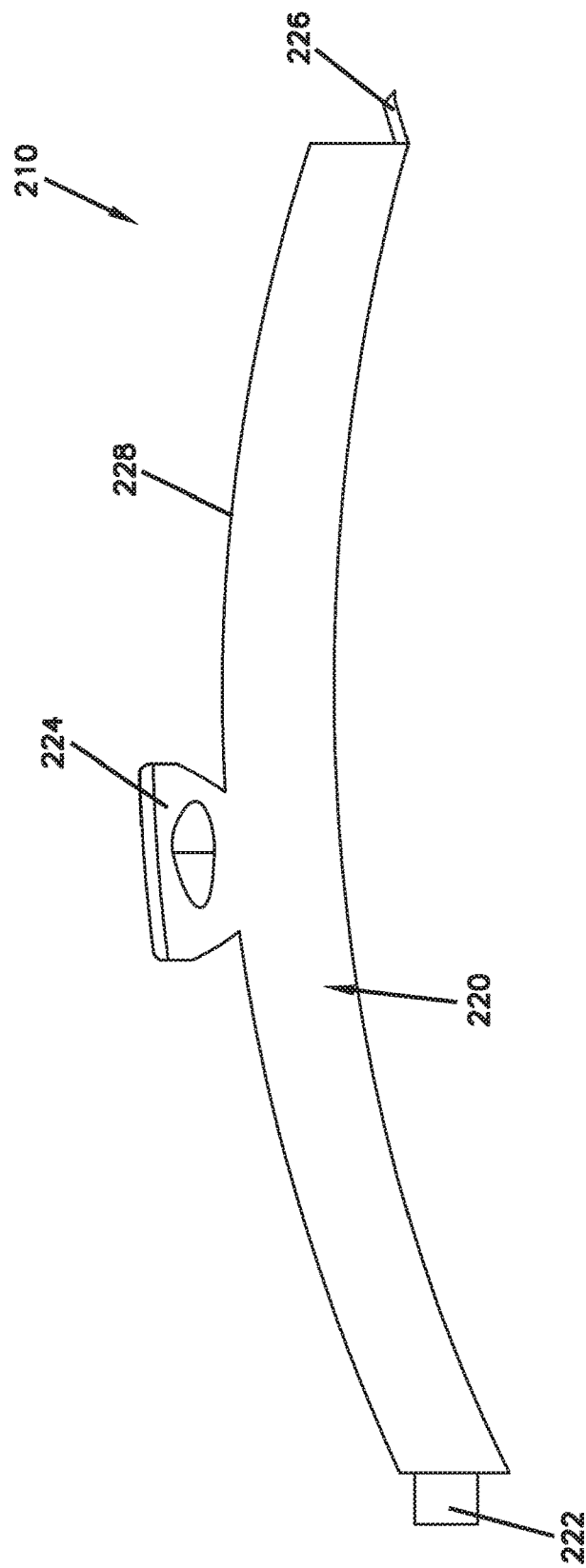
FIG. 12 is a side view of the light fixture of FIG. 8.
Figure 13:
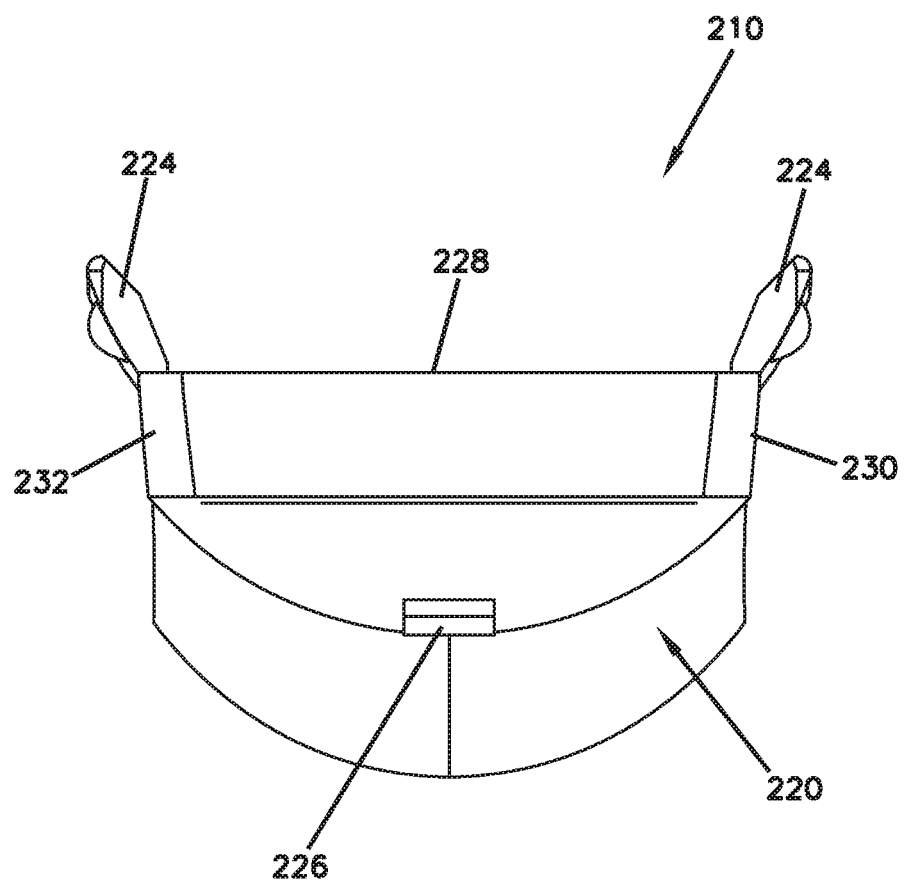
FIG. 13 is an end view of the light fixture of FIG. 8.
Figure 14:
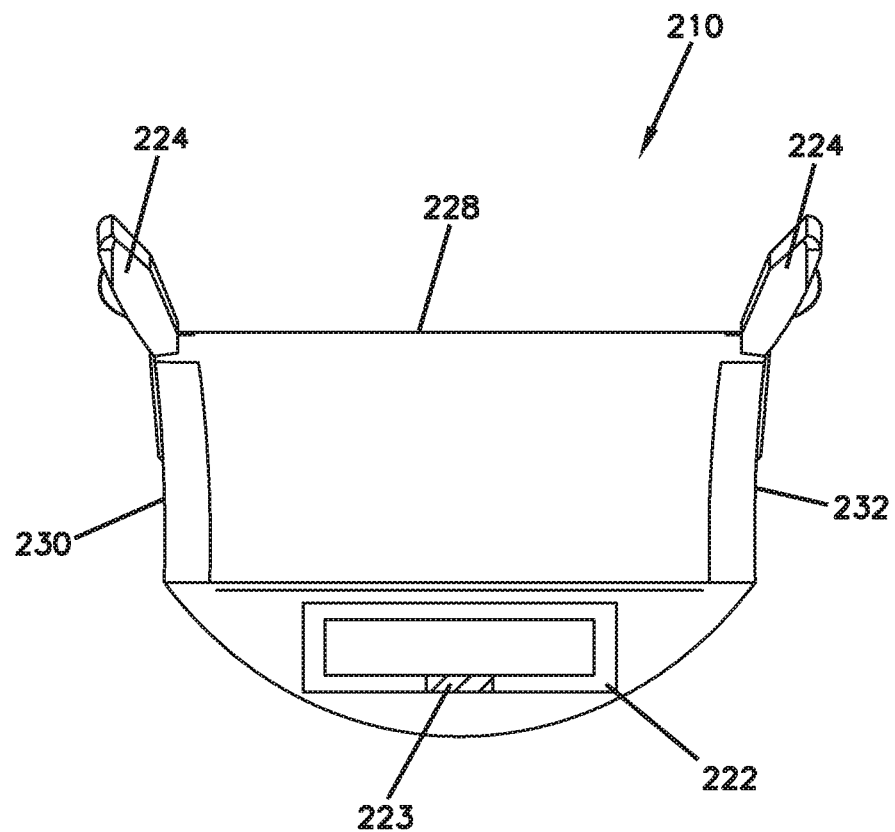
FIG. 14 is another end view of the light fixture of FIG. 8.

FIGS. 10-14 show the light fixture 210 removed from the faucet 200. FIGS. 10-11 shows a front and a rear perspective view of the light fixture 210, respectively. FIG. 12 shows a side view of the light fixture 210. FIG. 13 shows a front view of the light fixture, and FIG. 14 shows a rear view of the light fixture.

As noted above, in some examples, the light fixture 210 is removable from the faucet 200 to allow for easy serviceability. The light fixture 210 can include at least a housing 220 and a light 221. In the depicted embodiment, the light fixture 210 also includes a power connecter 222, a pair of flexible biasing bumpers 224, and a tab 226. In some examples, the light fixture 210 can be mounted within, and removed from, the faucet 210 without the use of tools. In some examples, the light fixture 210 can be secured within the faucet with at least one fastener (not shown). In some examples, the light fixture 210 can be movably mounted within the faucet 200 to permit pivotal relative movement with respect to a mounting location 211 to allow the user to aim the light fixture 210, separate from the faucet 200.

The housing 220 is configured to surround and hold the light 221. The housing 220 of the light fixture 210 can have a variety of different shapes to accommodate both the shape of the light 221 and/or the mounting location 211 of the light fixture 210 on the faucet. In some examples, similar to the light fixtures 75, 116 described above, the housing 220 can have a generally elongate shape having a length that is greater than a width. In some examples, the housing 220 can have a generally curved shape to match the mounting location 211 on the faucet 200. Further, the housing 220 can be sealed to prevent water from reaching the light 221. In some examples, the housing 220 is constructed from a plastic material. In other examples, the housing 220 is constructed from a metal material.

The light 221, shown schematically, can be any of a variety of light sources capable of emitting light when power is received. As noted above, the light 221 can be at least one light emitting diode. In other examples, the light 221 is a plurality of light emitting diodes. In other examples still, the light 221 is a plurality of light emitting diodes positioned on a single circuit board such as a strip or ribbon. In other examples still, the light 221 can include a light tube. In some examples, the light 221 can include at least one optical fiber.

The power connector 222 can be configured to connect the light fixture 210 to a power source 219 (shown in FIG. 9) via power leads 217. In some examples, the power connector 222 can have a quick connect feature 223, shown schematically, to allow for easy connection with the power source 219 via the power leads 217. The quick connect feature 223 can be a magnetic component capable of removably magnetically coupling to power leads 217. In other examples, the quick connect feature 223 of the power connector 222 can include at least one prong and/or at least one receptacle configured to mate with the power leads 217. It is contemplated to be within the scope of the present disclosure, that the quick connect feature 223 of the power connector 222 can be of a variety of different types to aid in connecting the power connector 222 with the power leads 217 without the need for directly wiring the power leads 217 to the power connector 222.

In some examples, the light fixture 210 can include an on-board power source 227 (shown schematically), such as a battery, to power the light 221 of the light fixture in case of a loss of power from the power leads 217. In other examples, the on-board power source 227 can power the light fixture 218 during normal operation conditions, instead of using power leads 217. In some examples, the user can configure the light fixture 210 to use power from the on-board power source 227 and/or the power leads 217.

The flexible biasing bumpers 224 are configured to help position the light fixture 210 in the mounting location 211 on the faucet 200. As shown in FIGS. 13-14, the flexible biasing bumpers 224 can extend in a direction above a top side 228 of housing 220 and partially toward each side 230, 232. In some examples, the flexible biasing bumpers 224 have memory and can be temporarily deflected inward by the user when installing or removing the light fixture 210 from the faucet 200. In some examples, the flexible biasing bumpers 224 grasp the faucet 200 at the mounting location 211. In some examples, the flexible biasing bumpers 224 are constructed from a rubber material. In other examples, the flexible biasing bumpers 224 are constructed from a plastic material.

Like the flexible biasing bumpers 224, the tab 226 can be flexible and be configured to help position the light fixture 210 in the mounting location 211 on the faucet 200. In some examples, the tab 226 is positioned on the housing 220, opposite the power connector 222. In other examples, the housing 220 can include a plurality of tabs 226 positioned elsewhere on the housing 220 to aid in securing and positioning the light fixture 218 within the mounting location 211 of the faucet 200. In some examples, the tab 226 can include an accessible portion 234 that can be operated to release the light fixture 210 from the mounting location 211 by the user when light fixture 210 is positioned within the faucet 200.

Figure 15:
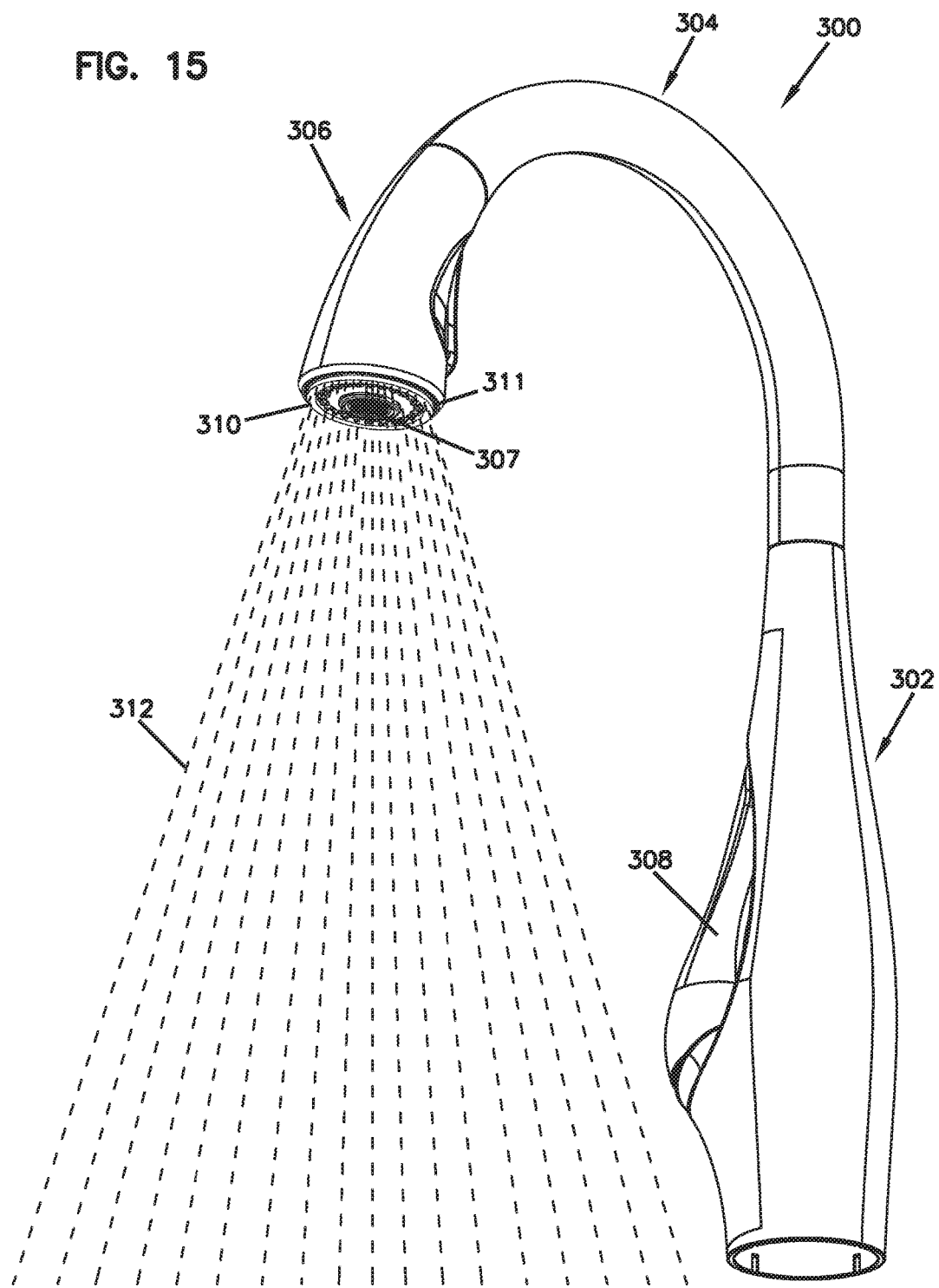
FIG. 15 is a perspective view of a faucet with integrated lighting, according to one embodiment of the present disclosure.
Figure 16:
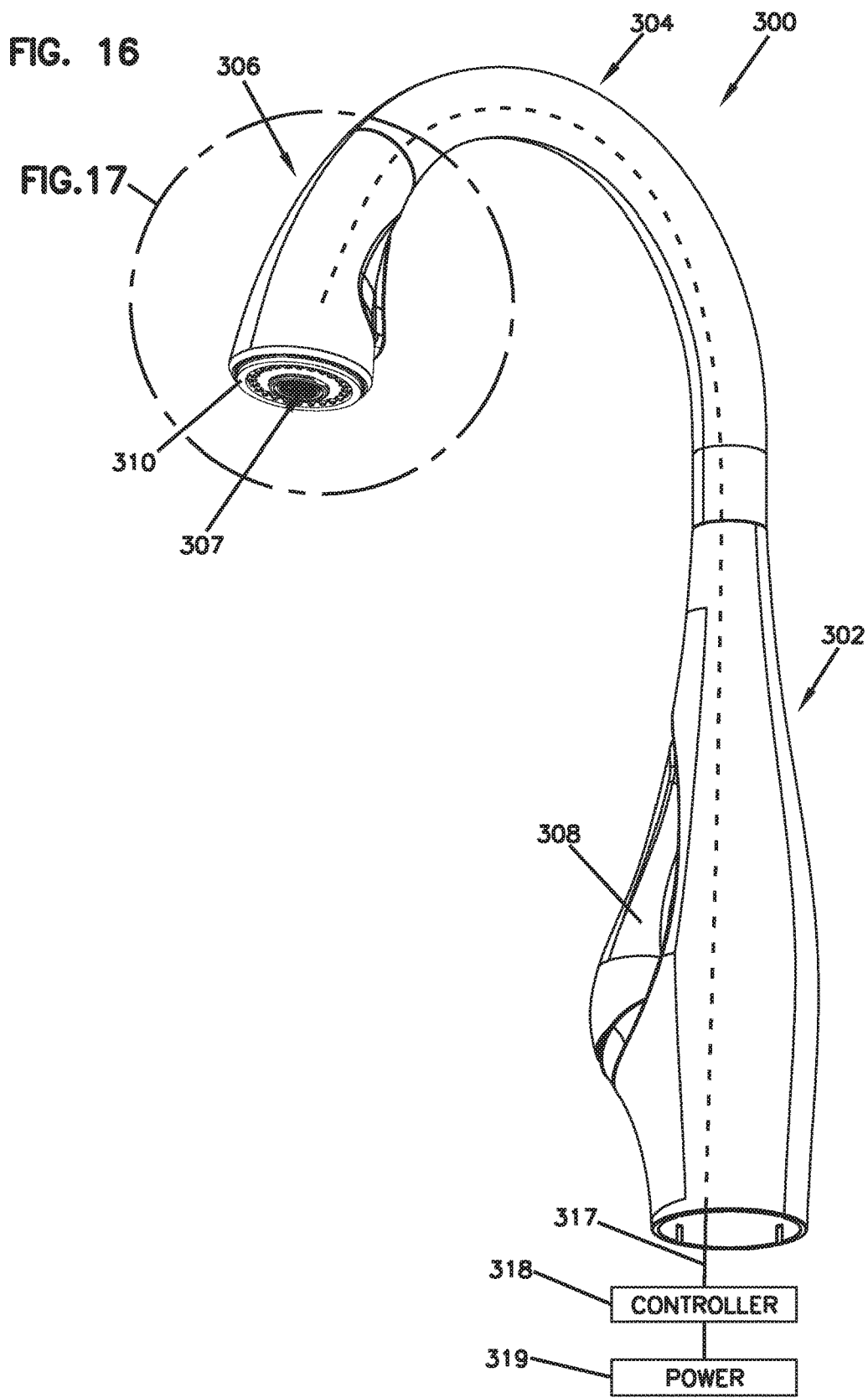
FIG. 16 is another perspective view of the faucet of FIG. 15.
Figure 17:
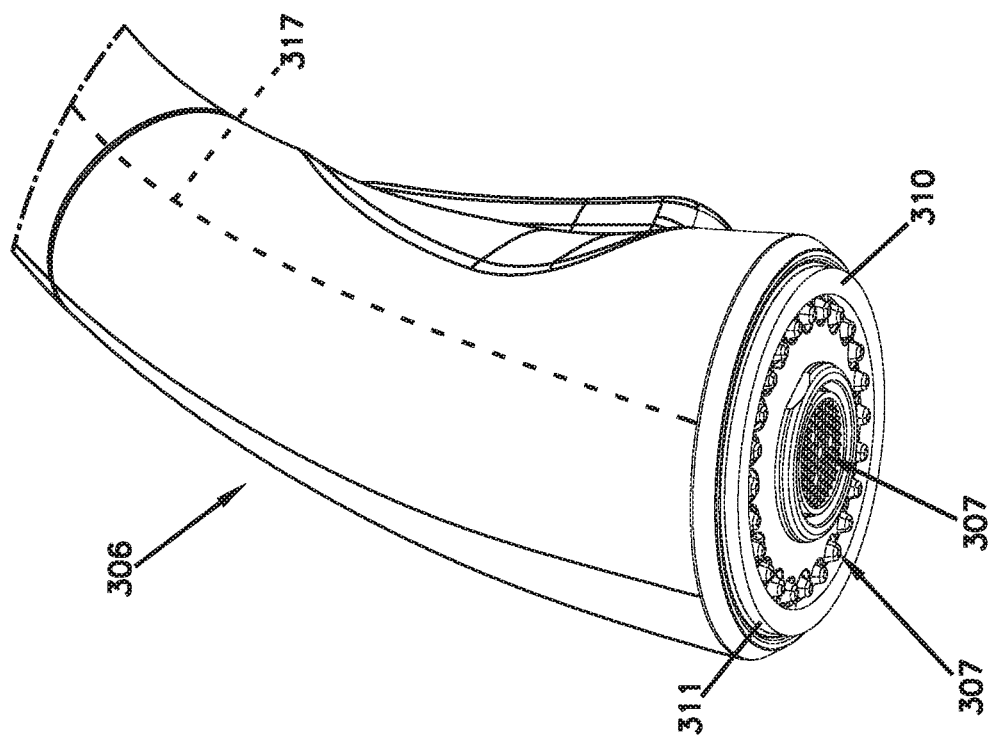
FIG. 17 is a perspective view of a spray head of the faucet of FIG. 15.

FIGS. 15-17 show a faucet 300 according to another embodiment of the present disclosure. The faucet 300 is substantially similar to the faucets 2, 109, and 200 disclosed above. The faucet 300 includes a body 302, a neck 304, a spray head 306, an optional first input device 308, and a light fixture 310. In some examples, the faucet 300 does not include a first input device 308 and is instead controlled by sensor (i.e., touch, voice, motion, etc.). The faucet 300 is configured to deliver water and lighting, either in the form of UV light or visible light, and is configured be controlled in a similar manner to the previously discussed faucets 2, 109, 200. The faucet 300 is securable to a counter using an optional deck plate and mounting hardware (not shown).

The light fixture 310 is configured to be positioned within a portion of the faucet 300 at a mounting location 311. As shown, the light fixture 310 can be mounted to spray head 306. In some examples, the mounting location 311 is an opening in the spray head 306. In some examples, the light fixture 310 is configured to emit at least one of visible light and UV light in a coverage pattern 312. In some examples, the light fixture 210 can emit both visible light and UV light, either at the same time or individually, based on particular inputs received by the user. The light fixture 310 can be connected to a controller 318 and power source 319 via leads 317. In some examples, the controller 318 is substantially similar, both in structure and function, to the controller 218 above.

As shown in FIG. 17, the light fixture 310 can be positioned at least partially around a water nozzle 307 disposed in the spray head 306. In other examples, the light fixture 310 is positioned inside the water nozzle 307. The water nozzle 307 is configured to dispense water therefrom. In some examples, the light fixture 310 can be a ring. In other examples, the light fixture 310 is a circular insert.

EXAMPLES

In one example of the present disclosure, a faucet is disclosed. The faucet can include a body that has a first end and a second end. The first end is securable to a surface and the second end is spaced from the first end. The faucet can include a neck that has a first end and a second end. The first end of the neck is coupled to the second end of the body and the second end of the neck is cantilevered from the body. The faucet can include a light fixture secured in an exterior portion of the neck between the first end and the second end of the neck. The faucet can include a spray head coupled to the second end of the neck.

In any of the examples disclosed herein, the light fixture can selectively emit at least one of visible light and ultraviolet light.

In any of the examples disclosed herein, when the light fixture is configured to emit ultraviolet light, the ultraviolet light can have a wavelength between 100 nm and 350 nm.

In any of the examples disclosed herein, the light fixture is selectively activated to illuminate at a plurality of user-selectable intensity levels.

In any of the examples disclosed herein, the light fixture can include a plurality of light emitting diodes.

In any of the examples disclosed herein, the light fixture can include a first timer feature.

In any of the examples disclosed herein, the light fixture can be toggled from an ON state to an OFF state after a predetermined amount of time has elapsed, when in the ON state, the light fixture emits light and, when in the OFF state, the light fixture does not emit light.

In any of the examples disclosed herein, the body can be secured to a surface.

In any of the examples disclosed herein, the body can be secured to a counter.

In any of the examples disclosed herein, the faucet includes an opening formed in a portion of the neck facing a plane of the counter.

In any of the examples disclosed herein, the light fixture can be secured within an opening of the neck.

In any of the examples disclosed herein, the light fixture can be activated by at least one of a voice command, a user touch on a surface of the faucet, and a predetermined user gesture.

In any of the examples disclosed herein, the faucet can include a proximity sensor configured to sense at least one of a predetermined gesture and a user presence and thereby activate the light fixture.

In any of the examples disclosed herein, the faucet can include a cleaning mode. When in the cleaning mode, the light fixture emits ultraviolet light.

In any of the examples disclosed herein, a proximity sensor senses movement when the faucet is in a cleaning mode.

In any of the examples disclosed herein, a proximity sensor activates the light fixture to stop the light fixture from emitting light when in a cleaning mode.

In any of the examples disclosed herein, the neck can be curved with at least a portion of the light fixture within the curve.

In another example of the present disclosure, a faucet is disclosed. The faucet can include a body that has a first end and a second end. The first end is securable to a surface and the second end is spaced from the first end. The faucet can include a neck that has a first end and a second end. The first end of the neck is coupled to the second end of the body and the second end of the neck is cantilevered from the body. The neck can be movable with respect to the body. The faucet can include a spray head coupled to the second end of the neck, opposite the body. The faucet can include a light fixture secured to at least one of an exterior portion of the body, neck, and spray head. The faucet can include at least one input device that is configured to receive input from a user. Upon receipt of an input, the input device can activate the light fixture.

In any of the examples disclosed herein, at least one input device can selectively control a water volume of water emitted from the spray head.

In any of the examples disclosed herein, the light fixture can selectively emit at least one of visible light and ultraviolet light.

In any of the examples disclosed herein, the light fixture can be configured to selectively emit light at a plurality of intensities that are user-selectable via at least one control device.

In any of the examples disclosed herein, at least one input device is at least one of a lever, a button, a capacitive touch sensor, and a voice activated sensor.

In any of the examples disclosed herein, when at least one input device is a proximity sensor, the proximity sensor can be configured to sense at least one of a predetermined gesture and a user presence to activate the light fixture.

In another example of the present disclosure, a faucet is disclosed. The faucet can include a body with a base that is configured for attachment to a counter. The body can include a top, opposite the base, suspended above the counter. The faucet can include an input device that is configured to receive input from a user regarding at least one of a water volume and a water temperature. The faucet can include a neck that has a first end attached to the top of the body, a mid-section that is defined by a curvature, and a second end opposite the first end. The faucet can include a spray head attached to the second end of the neck. The spray head can be configured for detachment from the neck. The faucet can include a light fixture secured to the neck and oriented facing the counter between the body and the spray head.

In any of the examples disclosed herein, a second input device can be configured to activate the light fixture based upon a predetermined input.

In any of the examples disclosed herein, a second input device includes a proximity sensor and the predetermined input includes motion.

In any of the examples disclosed herein, the light fixture can selectively emit at least one of visible light and ultraviolet light.

In any of the examples disclosed herein, the light fixture can include a plurality of light emitting diodes.

Although the present disclosure has been described with reference to particular means, materials and embodiments, from the foregoing description, one skilled in the art can easily ascertain the essential characteristics of the present disclosure and various changes and modifications may be made to adapt the various uses and -characteristics without departing from the spirit and scope of the present invention as set forth in the following claims.

We claim:

1. A faucet comprising:
a body having a first end and a second end, the first end being securable to a surface and the second end being spaced from the first end;
a neck having a first end, a second end, and a recess located between the first end and the second end, the first end of the neck being coupled to the second end of the body and the second end of the neck being cantilevered from the body;
a light fixture secured in an exterior portion of the neck between the first end and the second end of the neck, wherein the light fixture is mounted within the recess of the neck; and
a spray head coupled to the second end of the neck.

2. The faucet according to claim 1, wherein the light fixture selectively emits at least one of visible light and ultraviolet light.

3. The faucet according to claim 2, wherein, when the light fixture is configured to emit ultraviolet light, the ultraviolet light has a wavelength between 100 nm and 350 nm.

4. The faucet according to claim 1, wherein the light fixture is selectively activated to illuminate at a plurality of user-selectable intensity levels.

5. The faucet according to claim 1, wherein the light fixture includes a plurality of light emitting diodes.

6. The faucet according to claim 1, wherein the light fixture includes a first timer feature, wherein the light fixture is toggled from an ON state to an OFF state after a predetermined amount of time has elapsed, wherein, when in the ON state, the light fixture emits light and, when in the OFF state, the light fixture does not emit light.

7. The faucet according to claim 1, wherein the body is secured to a surface, the surface being a counter, wherein the faucet further comprises an opening formed in a portion of the neck facing a plane of the counter, wherein the light fixture is secured within the opening of the neck.

8. The faucet according to claim 1, wherein the light fixture is activated by at least one of a voice command, a user touch on a surface of the faucet, and a predetermined user gesture.

9. The faucet according to claim 1, further comprising a proximity sensor configured to sense at least one of a predetermined gesture and a user presence and thereby activate the light fixture.

10. The faucet according to claim 9, further comprising a cleaning mode, wherein, when in the cleaning mode, the light fixture emits ultraviolet light, and wherein, when the proximity sensor senses movement when the faucet is in the cleaning mode, the proximity sensor activates the light fixture to stop the light fixture from emitting light.

11. The faucet according to claim 1, wherein the neck is curved with at least a portion of the light fixture within the curve.

12. A light-providing faucet comprising:
a body having a first end and a second end, the first end being securable to a surface and the second end being spaced from the first end;
a neck having a first end and a second end, the first end of the neck being coupled to the second end of the body and the second end of the neck being cantilevered from the body, wherein the neck is movable with respect to the body;
a spray head coupled to the second end of the neck, opposite the body;
a light fixture mounted within a recess of at least one of an exterior of the body or neck;
at least one input device configured to receive input from a user; wherein upon receipt of an input, the input device activates the light fixture.

13. The faucet according to claim 12, wherein the at least one input device can also selectively control a water volume of water emitted from the spray head.

14. The faucet according to claim 12, wherein the light fixture selectively emits at least one of visible light and ultraviolet light.

15. The faucet according to claim 12, wherein the light fixture is configured to selectively emit light at a plurality of intensities that are user-selectable via the at least one control device.

16. The faucet according to claim 12, wherein the at least one input device is at least one of a lever, a button, a proximity sensor, a capacitive touch sensor, and a voice activated sensor.

17. The faucet according to claim 16, wherein, when the at least one input device is a proximity sensor, the proximity sensor is configured to sense at least one of a predetermined gesture and a user presence to activate the light fixture.

18. A faucet comprising:
a body with a base configured for attachment to a counter and a top opposite the base suspended above the counter;
an input device configured to receive input from a user regarding at least one of a water volume and a water temperature;
a neck with a first end attached to the top of the body, a mid-section defined by a curvature, and a second end opposite the first end;
a spray head attached to the second end of the neck and configured for detachment from the neck;
a light fixture secured to the neck and oriented facing the counter between the body and the spray head, wherein the light fixture has a curved shape that matches the curvature of the mid-section of the neck.

19. The faucet of claim 18, further comprising a second input device configured to activate the light fixture based upon a predetermined input.

20. The faucet of claim 19, wherein the second input device includes a proximity sensor and the predetermined input includes motion.

21. The faucet according to claim 18, wherein the light fixture selectively emits at least one of visible light and ultraviolet light, and wherein the light fixture includes a plurality of light emitting diodes.

* * * * *